United States Patent [19]

Janitschke et al.

[11] 4,431,844
[45] Feb. 14, 1984

[54] PREPARATION OF POLYUNSATURATED KETONES

[75] Inventors: Lothar Janitschke, Kleinniedesheim; Werner Hoffmann, Neuhofen; Lothar Arnold, Heidelberg; Manfred Stroezel, Ilvesheim; Hans-Jüergen Scheiper, Mutterstadt, all of Fed. Rep. of Germany

[73] Assignee: BASF Aktiengesellschaft, Rheinland-Pfalz, Fed. Rep. of Germany

[21] Appl. No.: 361,249

[22] Filed: Mar. 24, 1982

[30] Foreign Application Priority Data

Apr. 8, 1981 [DE] Fed. Rep. of Germany ....... 3114071

[51] Int. Cl.³ .................................................. C07C 45/45
[52] U.S. Cl. ................................... 568/390; 568/417
[58] Field of Search ............................... 508/390, 345

[56] References Cited

U.S. PATENT DOCUMENTS 2,957,027 10/1960 Beets et al. ........................... 568/390
3,470,209 9/1969 Lamparsky et al. ................. 568/390
3,840,601 10/1974 Gradeff .
3,975,451 8/1976 Fujita et al. ........................ 568/390

FOREIGN PATENT DOCUMENTS

2637428          Fed. Rep. of Germany ...... 568/390
79483 11/1971    Fed. Rep. of Germany ...... 568/390
3637428 2/1978   Fed. Rep. of Germany ...... 568/390

OTHER PUBLICATIONS

Sause et al., Chem. Abst., vol. 71, #38,354 (1969).

*Primary Examiner*—James H. Reamer
*Attorney, Agent, or Firm*—Oblon, Fisher, Spivak, McClelland & Maier

[57] ABSTRACT

An improved process for the preparation of unsaturated ketones of the general formula I

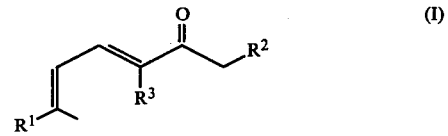

where $R^1$ is —$CH_3$,

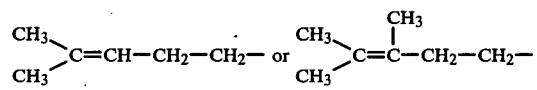

and $R^2$ and $R^3$ are different and each is H or —$CH_3$, by reacting an aldehyde of the general formula II

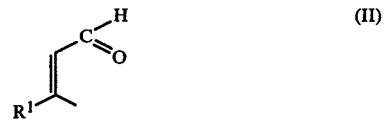

with a molar excess of acetone or methyl ethyl ketone at an elevated temperature in the presence of an aqueous alkali metal hydroxide solution, wherein (a) all the reactants are mixed thoroughly, (b) the temperature is kept at from 10 to 120° C. above the boiling point of the lowest-boiling component and (c) the pressure is kept at from p to 100 bar, where p is the vapor pressure of the mixture at the reaction temperature.

The products methylpseudoionone, dimethylpseudoionone, pseudoirone, methylpseudoirone and dimethylpseudoirone are useful scents and scent intermediates. In addition, pseudoionone is an important intermediate for the industrial preparation of vitamin A, and 6-methylhepta-3,5-dien-2-one is a sought-after aromatic.

11 Claims, No Drawings

PREPARATION OF POLYUNSATURATED KETONES

The present invention relates to an improved process for the preparation of polyunsaturated ketones, in particular of compounds such as 6-methyl-hepta-3,5-dien-2-one, pseudoionone, methylpseudoionone, dimethylpseudoionone, pseudoirone, methylpseudoirone and dimethylpseudoirone, which are scents and scent intermediates of great economic interest. Pseudoionone is also an important intermediate for the industrial preparation of vitamin A, and 6-methyl-hepta-3,5-dien-2-one is a sought-after aromatic.

Because of their industrial importance, there has been no lack of attempts to prepare these compounds by a very advantageous route. Countless processes for their preparation have therefore been disclosed, of which only those most closely related to the novel process will be described in the text which follows.

For example, Arosov et al. (Soviet Union Patent No. 138,612 of 1960) discloses that a 53% yield of 6-methyl-hepta-3,5-dien-2-one is obtained when a mixture of 3-methyl-but-2-en-1-al and water (as is obtained in the oxidation of 3-methyl-but-2-en-1-ol) is added to a mixture of 20 g of NaOH and 160 ml of dry acetone, with cooling. The yield is unsatisfactory for an industrial process.

R. Fischer et al. (German Laid-Open Application DOS No. 2,150,992 of 1971) disclose that 3-methyl-but-2-en-1-al can be condensed with acetone or methyl ethyl ketone in a molar ratio of about 1:3 at 180° C. and under 45 bar in the presence of ZnO in the course of 3 hours to give, respectively, 93% of 6-methyl-hepta-3,5-dien-2-one and 88% of 7-methyl-octa-4,6-dien-3-one in each case, based on the 3-methyl-but-2-en-1-al reached, with a conversion of 76 and 68% respectively. The disadvantages of this process are long reaction times together with low conversions, which result in low space/time yields.

Numerous methods for the preparation of pseudoionone from citral, which are based on the condensation of the latter with acetone in the presence of a base in an aqueous or non-aqueous solvent, have been disclosed. In any anhydrous medium, an alkali metal alcoholate or a phenolate is used as the condensing agent and an alcohol or benzene is used as the solvent (Russel et al, Org. Synth. 3, 380–384, and Czech Patent No. 85,207 of 1966).

The use of an alcoholate or phenolate requires separate preparation of this compound and requires all the reactants to be very dry, which makes the reaction very expensive and is not particularly advantageous in industrial production.

Processes for condensing citral with acetone in an aqueous solvent in which a sulfite (cf. German Democratic Republic Pat. No. 28,759 of 1960) or an alkali metal hydroxide is used as the condensing agent avoid these disadvantages, but give unsatisfactory yields of pseudoionone and lead to impurities which are difficult to remove.

Condensation of citral with acetone in the presence of an aqueous solution of a base is a cheaper variant of this process. Several such variants are known, which differ in the ratio of the components, in temperature and/or in reaction time. Our description here is restricted to the most advantageous process to date. Thus, Chem. Abstract 71 (1969) P 38 354X discloses the reaction of citral with a large excess of acetone in the presence of very dilute aqueous sodium hydroxide solution at from 30° to 40° C. to give, in 1.5 hours at 40° C., a yield of 90% of pseudoionone. The disadvantage of this process is that the reaction medium must be extremely dilute in order to suppress undesirable side reactions, which means that on the one hand only very low space/time yields are achieved and on the other hand both the energy consumption during evaporation of the acetone from the reaction mixture (the mixture does not separate into phases under the above conditions), and the expense of extraction from the very dilute solution are extremely high.

Soviet Union Pat. No. 704,938 of 1978 proposes carrying out the reaction with a 15–20 fold excess of acetone and an acetone:water volume ratio in the reaction mixture of from 1:0.15 to 1:0.45 in order to avoid the disadvantages described. The yields achieved are good, but the chief disadvantage is the extremely long process time of from 2.5 to 5 hours, which means that the space/time yields achieved become very low.

Soviet Union Pat. No. 546,603 of 1974 proposes carrying out the base-catalyzed reaction of citral with acetone or methyl ethyl ketone in the presence of condensation products of citral with itself or of citral with the corresponding ketone in amounts of from 20 to 100%, based on the citral employed. The yields achieved in this process are also quite good, but again the disadvantage is the long reaction time. In Example 2, for instance, after a feed time of 2 hours, the mixture must be heated for another 3 hours, giving unsatisfactory space/time yields.

It is an object of the present invention to improve the process for the preparation of the unsaturated ketones of the general formula I by reaction of an α,β-unsaturated aldehyde with acetone or methyl ethyl ketone in the presence of aqueous alkali metal hydroxide solution so that the disadvantages of the conventional processes are avoided, ie. so that the unsaturated ketones are obtained in good yield, in a simple manner and with good space/time yields.

We have found that this object is achieved by a process for the preparation of unsaturated ketones of the general formula I

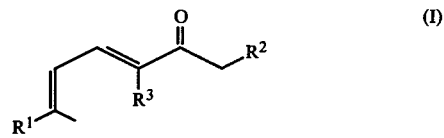

where $R^1$ is —CH$_3$,

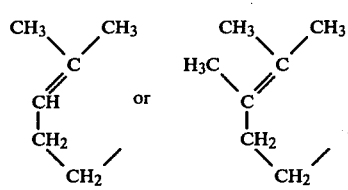

and $R^2$ and $R^3$ are each hydrogen or are different with one hydrogen and the other —CH$_3$, by reacting an aldehyde of the general formula II

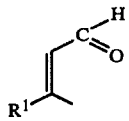

with a molar excess of a ketone of the general formula III

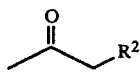

at an elevated temperature in the presence of an aqueous alkali metal hydroxide solution, wherein (a) all the reactants are mixed thoroughly, (b) the temperature is kept at from 10° to 120° C., preferably from 25° to 75° C., above the boiling point of the lowest-boiling component and (c) the pressure is kept at from p to 100 bar, where p is the vapor pressure of the mixture at the reaction temperature.

It is very surprising that the space/time yields in the reaction of the sensitive α,β-unsaturated aldehydes II with acetone or methyl ethyl ketone in the presence of aqueous alkali metal hydroxide solution can be improved to an exceptional degree under the conditions according to the invention without giving poorer yields of unsaturated ketones because of the more drastic conditions. Such reactions have hitherto generally been carried out at or below the reflux temperatures, and the need to warm the mixture was regarded as a disadvantage because of the associated losses of acetone and citral and because of the accelerated resinification of the reaction batch (cf. Soviet Union Pat. No. 704,938, column 3, lines 14–20). The severe prejudices against heating a reaction batch containing the aldehyde II, the ketone III and aqueous alkali metal hydroxide solution to a relatively high temperature are very understandable considering that it has been disclosed that α,β-unsaturated aldehydes have a strong tendency to undergo self-condensation and polymerization, especially in the presence of alkali (cf., for example, H. Labbé, Bull.Soc. Chim. Fr. 21 (1899), 407 and Thomas, Helv. Chim. Acta 59 (1976), 2261–67).

Suitable aldehydes of the formula II are 3-methyl-but-2-en-1-al, 3,7-dimethyl-octa-2,6-dien-1-al (citral) and 3,6,7-trimethyl-octa-2,6-dien-1-al. These compounds are known, and can be prepared in a conventional manner.

The ketones used, acetone and methyl ethyl ketone, are commercial compounds and are generally used in molar excess, in particular in amounts of from 8 to 30, preferably from 9 to 15, moles per mole of aldehyde. Smaller amounts lead to an increase in the residence time and losses of yield. Larger amounts confer no further economic advantage. Unreacted ketone is recovered during working up and can be reused.

The aqueous alkali metal hydroxide solution is generally a 0.005–20% strength by weight aqueous solution of NaOH or KOH. An approximately 0.1–15% strength by weight solution, in particular an approximately 0.3–7% strength by weight solution, is preferred for the reaction with acetone, and a 0.5–20% strength by weight solution is preferred for the reaction with methyl ethyl ketone.

From 0.001 to 0.6 mole, preferably from 0.005 to 0.5 mole, of alkali metal hydroxide is generally used per mole of aldehyde.

The amount of alkali required is determined, inter alia, by the acid content of the aldehyde used.

The process according to the invention is carried out by reacting a mixture of an aldehyde II and a ketone III with the aqueous alkali metal hydroxide solution, while mixing thoroughly, either at a constant temperature or within a certain temperature range under the reaction pressure.

If the reaction is to proceed advantageously, it is very important that the components are mixed thoroughly so that the mixture, which generally comprises two phases, does not demix. Thorough mixing of the catalyst solution and reactants can be effected by means of any apparatus conventionally used for this purpose, such as a stirred kettle, a static mixer (eg. a Sulzer or Kenics mixer), a dynamic mixer (eg. a high-speed pump or high-speed stirrer) or a mixing nozzle, provided this apparatus permits such thorough mixing that the diameter of the droplets in the reaction mixture is not more than 1 mm, preferably not more than 0.1 mm. If the reactor is designed so that no demixing takes place during the reaction, the reaction mixture can be thoroughly mixed by means of mixing nozzles or other mixing fitments before entry into the reaction. However, the reactor can also be designed to serve simultaneously as a mixer. Which mixer is most advantageous depends on the type of reaction procedure and reaction vessel. A procedure in which the reaction mixture flows through the reactor with a constant drop size and constant drop flow is very advantageous.

A further essential feature of the process according to the invention is that the reaction is carried out above the boiling point of the reaction mixture under normal pressure, and therefore also under a pressure above the vapor pressure of the reaction mixture at the boiling point. In practice, the temperature is from 10° to 120° C., preferably from 25° to 75° C., above the boiling point of the lowest-boiling component. In the case of acetone, the reaction is carried out at from 65° to 180° C., preferably from 80° to 130° C., and in the case of methyl ethyl ketone at from 90° to 200° C., preferably from 105° to 155° C.

The pressure can be the vapor pressure of the mixture at the reaction temperature, or increased to not more than 100 bar, preferably to not more than 20 bar. Especially in the continuous procedure, it is advantageous if the pressure is set to above the vapor pressure by introducing an inert gas.

Residence times of less than 45 minutes, in particular of less than 30 minutes, are sufficient to achieve virtually quantitative conversion under the conditions according to the invention. Residence times of from 4 to 10 minutes are the rule in the case of a continuous procedure in a reaction tube using preheated starting materials.

Taking into consideration the fact that residence times of from 2 to 8 hours or more are usual for these reactions by conventional processes, drastic increases in the space/time yields compared with the atmospheric pressure procedure result in the process according to the invention.

The process can be carried out continuously or batchwise. The continuous procedure is particularly advantageous, and can be effected in several reaction vessels connected in series, or in one reaction column. However, tube reactors with suitable dimensions, especially those in which a sufficiently turbulent flow prevails under the reaction conditions so that the two-phase reaction mixture does not demix inside the reactor, are preferred.

In a particularly advantageous procedure, the catalyst solution, which may be preheated, is added to a preheated mixture of aldehyde II and ketone III under the reaction conditions. In this way, optimum reaction times may be achieved.

After the mixture has left the condensation reactor, it is neutralized with a cheap organic acid, such as acetic acid, or a cheap inorganic acid, such as sulfuric acid. If sulfuric acid is used, it may be advantageous to choose an acid concentration of less than 10%, in particular less than 3%, in order to prevent precipitation of sodium sulfate. In principle, all acids, including acidic ion exchangers, are suitable.

However, after the reaction mixture has left the condensation reactor, it is possible to free it from most of the alkali metal hydroxide solution in a phase separation vessel before it is neutralized with an acid. The alkali metal hydroxide solution recovered can then be reused in the reaction.

The reaction mixture is then further worked up by distillation of the ketone III, during which, preferably, only a certain amount of the water is also distilled off and the remainder holds in solution the salts formed during neutralization. This removal of the ketone III by distillation is also particularly advantageous if the process according to the invention is carried out industrially, since the reaction mixture is already hot, because of the high reactor temperature, and the ketone rapidly vaporizes.

The aqueous salt-containing lower phase of the resulting distillation residue is separated off. Very pure product is isolated from the upper organic phase by distillation. Unreacted aldehyde II is obtained in the distillation first runnings. The aldehyde II and ketone III recovered can be reused for the reaction.

The yield of ketone I is up to 95% (calculated as 100% pure ketone), based on 100% pure aldehyde II employed, or up to 100%, based on aldehyde II reacted.

The compounds prepared according to the invention are useful scents or scent intermediates. Pseudoionone is also an important intermediate in the industrial synthesis of vitamin A, and 6-methyl-hepta-3,5-dien-2-one is a sought-after aromatic.

The particular advantage of the process according to the invention is that the residence time for the reactants in the reactor can be drastically reduced under the reaction conditions according to the invention, without a decrease, and in some cases even with an increase, in the yield, the space/time yield for the reaction being similarly drastically increased.

EXAMPLE 1

Continuous preparation of 6,10-dimethyl-undeca-3,5,9-trien-2-one (pseudoionone; Ia)

In each case the amount of a 4.76% strength aqueous NaOH solution given in the Table which follows was dispersed, within a liquid/liquid mixing nozzle, in a mixture of citral (IIa) and acetone (IIIa) (molar ratio 10:1; for the amounts, see the Table) which had been preheated to 90° C., and the thoroughly mixed two-phase liquid was pumped, from the top downwards, through a 480 ml tube reactor (tube: 24 mm diameter, 1,200 mm in length) with a heating cartridge inserted centrally from the bottom. The reaction tube was uniformly heated so that the oven inlet temperature was about 90° C. and the oven outlet temperature was about 110° C. (for the exact values, cf. the Table). The reaction pressure was kept at 5 bar by a discharge control device.

After leaving the tube reactor, the mixture was cooled, let down to atmospheric pressure and neutralized.

After constant reaction conditions had been established, the feed and discharge were each measured over periods of 1 hour for the purpose of determining the yield. To do this, the acetone (containing water) was first distilled off from the neutralized discharged mixture under atmospheric pressure (bath temperature: 100° C.), the aqueous phase was separated off from the residue and the organic phase was distilled. Four fractions were collected under 0.1–0.01 mbar:

(1) Pressure: 0.1 mbar, bath temperature: not more than 120° C.; boiling point range: not more than 90° C.

(2) Pressure: 0.05 mbar, bath temperature: not more than 160° C.;

(3) Pressure: 0.05 mbar, bath temperature: not more than 190° C.;

(4) Pressure: 0.01 mbar, bath temperature: not more than 240° C.

The data, in each case based on 1 hour, are summarized in the Table which follows.

The purity of the citral used was about 90.2% (Examples a, b and f), 72.2% (Example c), 88.9% (Example d) and 87.5% (Example e). In Example e, 72.0% was the cis-isomer content and 15.8% was the trans-isomer content.

In Example f, the mixture was neutralized with 2.5% strength sulfuric acid at 60° C., and in the other Examples it was neutralized with glacial acetic acid at room temperature.

|  |  |  | Example | | | | | |
|---|---|---|---|---|---|---|---|---|
|  |  |  | a | b | c | d | e | f |
| Feeds | Citral | [g/h] | 735.5 | 827.1 | 986.9 | 1052.4 | 1141.4 | 1217.2 |
|  | (IIa) | [mole/h] | 4.36 | 4.90 | 4.68 | 6.14 | 6.56 | 7.21 |
|  | Acetone | [g/h] | 2531.4 | 2846.9 | 2720.8 | 3569.7 | 3811.4 | 4190.2 |
|  | (IIIa) | [mole/h] | 43.6 | 49.0 | 46.8 | 61.4 | 65.6 | 72.1 |
| aqueous | NaOH | [g/h] | 249.7 | 433.8 | 469.8 | 568.7 | 555.5 | 1058.0 |
|  | NaOH | [mole/h] | 0.297 | 0.516 | 0.559 | 0.677 | 0.661 | 1.26 |
| Reaction temperature |  | [°C.] | 89–109 | 90–111 | 88–108 | 90–110 | 89–110 | 103–131 |
| Residence time |  | [min] | 6.51 | 5.82 | 5.74 | 4.61 | 4.34 | 3.75 |
| Neutralized discharge |  | [g/h] | 2866.6 | 4075.0 | 4010.0 | 6350.0 | 5500 | 8000.0 |
| Acetone distilled off |  | [g/h] | 2400.0 | 2640.6 | 2436.7 | 3145.0 | 2805.0 | 4428.6 |

| | | Example | | | | | |
|---|---|---|---|---|---|---|---|
| | | a | b | c | d | e | f |
| Water separated off | [g/h] | 343.0 | 326.0 | 358.3 | 265.0 | 385.5 | 1371.4 |
| Organic residue | [g/h] | 1061.0 | 1091.3 | 1177.0 | 1575.5 | 1532.5 | 2122.3 |
| Fraction I amount | [g/h] | 155.0 | 242.7 | 203.7 | 147.5 | 164.5 | 333.7 |
| Ia | [%] | 40.8 | 63.1 | 36.6 | 49.0 | 32.4 | 54.2 |
| IIa | [%] | 15.5 | 9.6 | 16.5 | 24.2 | 21.2 | 6.3 |
| Fraction 2 amount | [g/h] | 635.0 | 575.3 | 658.7 | 1057.5 | 1000.0 | 989.7 |
| Ia | [%] | 98.9 | 97.9 | 95.2 | 96.2 | 95.5 | 97.8 |
| IIa | [%] | 0.2 | 0.3 | 1.1 | 1.9 | 1.4 | 0.3 |
| Fraction 3 amount | [g/h] | 25.0 | 42.3 | 33.3 | 33.5 | 89.0 | 69.1 |
| Ia | [%] | 98.1 | 99.9 | 89.5 | 84.4 | 79.5 | 97.2 |
| Fraction 4 amount | [g/h] | 24.3 | 79.3 | 74.7 | 26.5 | 24.5 | 121.7 |
| Ia | [%] | 7.2 | 26.1 | 10.5 | 12.9 | 27.2 | 20.3 |
| Residue | [g/h] | 158.7 | 113.3 | 86.3 | 266.5 | 200.0 | 581.1 |
| Total amount Ia (100% pure) | [mole/h] | 3.73 | 4.05 | 3.84 | 5.83 | 5.65 | 6.45 |
| Yield, based on citral employed | [%] | 85.6 | 82.7 | 82.1 | 95.0 | 86.1 | 89.5 |
| Conversion | [%] | 95.0 | 94.3 | 94.3 | 94.0 | 95.1 | 97.8 |
| Yield, based on citral reacted | [%] | 90.1 | 87.7 | 87.0 | 100 | 90.5 | 91.5 |

EXAMPLE 2

Preparation of 3,6,9-trimethyl-undeca-3,5,9-trien-2-one (iso-methylpseudoionone) and 7,11-dimethyl-dodeca-4,6,10-trien-3-one (n-methyl-pseudoionone)

22.8 g of approximately 92% pure citral (0.137 mole) and 108 g (1.5 mole) of methyl ethyl ketone were heated to 130° C. in an autoclave. When the reaction temperature had been reached, 12 ml of 10% strength sodium hydroxide solution were pumped in, and the reaction mixture was stirred thoroughly at 130° C. for 20 minutes. 40 ml of 10% strength aqueous acetic acid solution were then pumped in, and the autoclave was cooled to room temperature. After the two-phase reaction mixture had been let down to atmospheric pressure, it was taken up in 500 ml of n-hexane and the aqueous phase was separated off. The organic phase was washed with twice 250 ml of water and dried with anhydrous sodium sulfate.

The solvent was distilled off under 20 mbar and at a bath temperature of 50° C., and the residue (28.0 g) was distilled over a bridge at a bath temperature of 200° C. (boiling point=56—112° C./0.05 mm Hg). This procedure gave 21.8 g of a mixture which, according to its gas chromatogram, consisted of 3.6% of citral and 94.7% of iso-methylpseudoionone and n-methylpseudoionone as a cis/trans isomer mixture. The yield of 100% pure isomer mixture was 73.1%, based on 100% pure citral, with an iso-methylpseudoionone: n-methylpseudoionone isomer ratio of about 15:85.

We claim:

1. A process for the preparation of unsaturated ketones of formula I:

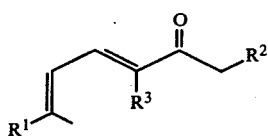

wherein $R^1$ is methyl,

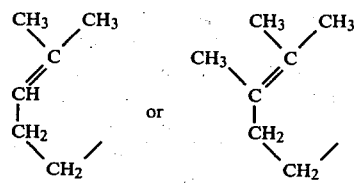

and $R^2$ and $R^3$ are both hydrogen or are different with one hydrogen and the other methyl, comprising:
reacting on aldehyde of formula II

with a molar excess of acetone or methylethylketone at an elevated temperature in the presence of an aqueous alkali metal hydroxide solution; wherein (a) all of the reactants, including the aqueous medium, generally existing as two liquid phases, are thoroughly mixed, (b) the temperature is maintained at a level from 10° to 120° C. above the boiling point of the lowest-boiling constituent of the reaction mixture, and (c) the pressure is maintained at a level from p to 100 bar, wherein p is the vapor pressure of the mixture of reaction ingredients at the reaction temperature.

2. The process of claim 1, wherein the temperature of the reaction is maintained at from 25° to 75° C. above the boiling point of the lowest-boiling component of the reaction mixture.

3. The process of claim 1, wherein, when said ketone reactant is acetone, the temperature of the reaction is maintained from 65° to 180° C.

4. The process of claim 3, wherein said temperature ranges from 80° to 130° C.

5. The process of claim 1, wherein, when said ketone reactant is methylethylketone, the temperature of the reaction ranges from 90° to 200° C.

6. The process of claim 5, wherein said temperature ranges from 105° to 155° C.

7. The process of claim 1, wherein said reaction is a continuous reaction which is essentially complete at a residence time of less than 45 minutes.

8. The process of claim 1, wherein said aldehyde of formula II is 3-methyl-but-2-en-1-al, 3,7-dimethyl-octa-2,6-dien-1-al or 3,6,7-trimethyl-octa-2,6-dien-1-al.

9. The process of claim 1, wherein the molar excess of said acetone or methylethylketone reactant is a molar excess of from 8 to 30 moles per mole of aldehyde reactant.

10. The process of claim 1, wherein the concentration of alkali metal hydroxide in said aqueous alkali metal hydroxide solution amounts to a 0.005–20% strength by weight solution.

11. The process of claim 10, wherein the amount of said aqueous alkali metal hydroxide solution used is that which provides from 0.001 to 0.6 mole of alkali metal hydroxide per mole of aldehyde reactant.

* * * * *